(12) United States Patent
Ah et al.

(10) Patent No.: US 8,529,750 B2
(45) Date of Patent: Sep. 10, 2013

(54) APPARATUS AND METHOD FOR DETECTING BIOMOLECULES

(75) Inventors: Chil-Seong Ah, Daejeon (KR); Ansoon Kim, Daejeon (KR); Chan-Woo Park, Daejeon (KR); Chang-Geun Ahn, Daejeon (KR); Jong-Heon Yang, Daejeon (KR); In-Bok Baek, Cheongju-si (KR); Taeyoub Kim, Seoul (KR); HyeKyoung Yang, Daejeon (KR); Gun-Yong Sung, Daejeon (KR); Seon-Hee Park, Daejeon (KR); Han-Young Yu, Daejeon (KR); Moon-Gyu Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 151 days.

(21) Appl. No.: 13/062,146

(22) PCT Filed: Nov. 20, 2008

(86) PCT No.: PCT/KR2008/006843
§ 371 (c)(1),
(2), (4) Date: Mar. 3, 2011

(87) PCT Pub. No.: WO2010/030057
PCT Pub. Date: Mar. 18, 2010

(65) Prior Publication Data
US 2011/0165557 A1 Jul. 7, 2011

(30) Foreign Application Priority Data
Sep. 10, 2008 (KR) ........................ 10-2008-0089237

(51) Int. Cl.
*G01N 27/414* (2006.01)
(52) U.S. Cl.
USPC ......... 205/789; 205/792; 257/253; 435/287.1

(58) Field of Classification Search
USPC ............... 257/253; 205/789, 792, 793.5; 422/82.01–82.03; 435/6, 285.12, 287.1, 435/287.2; 436/103–105, 150, 182; 506/1, 506/9
See application file for complete search history.

(56) References Cited

U.S. PATENT DOCUMENTS 5,827,482 A 10/1998 Shieh et al.
6,150,106 A 11/2000 Martin et al.
(Continued)

FOREIGN PATENT DOCUMENTS

EP 1843152 A1 10/2007
EP 1843157 A1 10/2007
(Continued)

OTHER PUBLICATIONS

Cui, Yi et al., "Nanowire Nanosensors for Highly Sensitive and Selective Detection of Biological and Chemical Species," Science, vol. 293:1289-1292 (2001).
(Continued)

*Primary Examiner* — J. Christopher Ball
(74) *Attorney, Agent, or Firm* — Nelson Mullins Riley & Scarborough LLP

(57) ABSTRACT

Provided are an apparatus and method for detecting biomolecules. The apparatus includes a FET having a substrate, a source electrode, a drain electrode, a channel region between the source and drain electrodes, and probe molecules fixed to the channel region, wherein the source and drain electrodes are separated on the substrate, a microfluid supplier selectively supplying one of a reference buffer solution of low ionic concentration and a reaction solution of high ionic concentration containing target molecules, to the channel region of the FET to which the probe molecules are fixed, and a biomolecule detector detecting the target molecules by measuring a first current value of the channel region of the FET, and a second current value of the channel region of the FET to which the target molecules and the probe molecules that bind to each other in the reaction solution of high ionic concentration are fixed.

11 Claims, 5 Drawing Sheets

(56) References Cited

U.S. PATENT DOCUMENTS

| | | |
|---|---|---|
| 2005/0170347 A1* | 8/2005 | Miyahara et al. ............ 435/6 |
| 2005/0191683 A1 | 9/2005 | Yoo et al. |
| 2006/0141474 A1 | 6/2006 | Miyahara et al. |
| 2007/0231211 A1 | 10/2007 | Yoo et al. |
| 2007/0235760 A1 | 10/2007 | Shim et al. |
| 2009/0153130 A1 | 6/2009 | Shim et al. |
| 2009/0208922 A1 | 8/2009 | Choi et al. |

FOREIGN PATENT DOCUMENTS

| | | |
|---|---|---|
| JP | 2005-077210 | 3/2005 |
| JP | 2007-139762 | 6/2007 |
| KR | 1020050087955 | 9/2005 |
| KR | 1020070054021 | 5/2007 |
| KR | 10-0732610 | 6/2007 |
| KR | 10-0738081 | 7/2007 |
| KR | 1020070101436 | 10/2007 |
| KR | 10-0773549 | 11/2007 |
| KR | 10-0773550 | 11/2007 |
| WO | 98/08082 A1 | 2/1998 |
| WO | 2007/066954 A1 | 6/2007 |

OTHER PUBLICATIONS

Stern, Eric et al., "Importance of the Debye Screening Length of Nanowire Field Effect Transistor Sensors," Nano Letters, vol. 7(11):3405-3409 (2007).

Stern, Eric et al., "Label-free immunodetection with CMOS-compatible semiconducting nanowires," Nature, vol. 455 (7127):519-522 (2007).

Zheng, Gengfeng et al., "Multiplexed electrical detection of cancer markers with nanowire sensor arrays," Nature Biotechnology, vol. 23(10):1294-1301 (2005).

* cited by examiner

| Si Substrate | Con of PSA | Concentration of Reaction Buffer (pH7.4) | Flow Rate | PSA Reaction Time | 5μmPB Wash | Conjugates Reaction Time | 5μm Wash | Au Nps /μm² | Remark (Relative Ratio) |
|---|---|---|---|---|---|---|---|---|---|
| a | 50ng/ml | 1XPBS | 25 μℓ/min | 30Minute | No | 1h | 3Minute | 473 | 1 |
| b | 50ng/ml | 1XPBS | 25 μℓ/min | 30Minute | 30Minute | 1h | 3Minute | 483 | 1.02 |
| c | 50ng/ml | 5μmPB | 25 μℓ/min | 30Minute | No | 1h | 3Minute | 411 | 1 |
| d | 50ng/ml | 5μmPB | 25 μℓ/min | 30Minute | 30Minute | 1h | 3Minute | 21 | 0.05 |

APPARATUS AND METHOD FOR DETECTING BIOMOLECULES

RELATED APPLICATION

This application is a 35 U.S.C. §371 national stage filing of PCT Application No. PCT/KR2008/006843 filed on Nov. 20, 2008, which claims priority to, and the benefit of, Korean Patent Application No. 10-2008-0089237 filed Sep. 10, 2008. The contents of the aforementioned applications are hereby incorporated by reference.

TECHNICAL FIELD

The present invention relates to an apparatus and method for detecting biomolecules, and more particularly to an apparatus and method for detecting biomolecules using a field effect transistor (FET).

The present invention has been derived from a research undertaken as a part of the information technology (IT) development business by Ministry of Knowledge Economy and Institute for Information Technology Advancement, Republic of Korea (Project management No.: 2005-S-007-03, Project title: Ubiquitous health care module system).

BACKGROUND ART

A transistor-based biosensor including a transistor is one of apparatuses for detecting biomolecules using an electrical signal. The transistor-based biosensor, which is fabricated through a semiconductor process, has such an advantageous merit as rapid switching of an electrical signal, and thus many studies are being conducted on the transistor-based biosensor.

In particular, an apparatus (or biosensor) for detecting biomolecules using a field effect transistor (FET) requires low cost and short time, and is compatible with IC/MEMS process easily.

In a biosensor using a FET, target molecules (or analyst molecules, analytes) bind to probe molecules (or receptor molecules, acceptors) in a channel region or a gate of the FET, so that the amount of current flowing through the channel region varies due to a variation in a surface charge transferred to the channel region of the FET. This is used to detect the target molecules.

The intensity of a current flowing through the channel region may vary because the Debye length of a surface charge varies according to an ionic strength of a solution, that is, ion concentration. Therefore, target molecules can be detected using the FET under condition that the ionic strength of an electrolyte solution containing the target molecules is smaller than a charge quantity of the target molecule.

Meanwhile, body fluids including biomolecules, e.g., blood, serum, plasma, urine, or saliva, have different ion concentration for each person, and have relatively high ionic strength. Therefore, it is difficult to detect biomolecules by providing the biomolecules to the channel region of the FET directly. Moreover, even though the biomolecules are detected by measuring the current intensity of the channel region, the reliability and re-producibility become poor. Consequently, a buffer solution, which maintains the ion concentration constantly, is required to detect the biomolecules. Alternatively, body fluids containing the biomolecules should be diluted to detect the biomolecules. That is, typical apparatuses for detecting biomolecules using a FET can detect the biomolecules only if the solution has a low ionic strength.

DISCLOSURE OF INVENTION

Technical Problem

The present invention provides an apparatus for detecting biomolecules in a solution having a high ionic strength.

The present invention also provides a method for detecting biomolecules in a solution having a high ionic strength.

The object of the present invention is not limited to the aforesaid, but other objects not described herein will be clearly understood by those skilled in the art from following description.

Technical Solution

Embodiments of the present invention provide apparatuses for detecting biomolecules including: a field effect transistor (FET) comprising a substrate, a source electrode, a drain electrode, a channel region between the source and drain electrodes, and probe molecules fixed to the channel region, wherein the source and drain electrodes are space apart from each other on the substrate; a microfluid supplier selectively supplying one of a reference buffer solution of low ionic concentration and a reaction solution of high ionic concentration containing target molecules, to the channel region of the FET to which the probe molecules are fixed; and a biomolecule detector detecting the target molecules by measuring a first current value of the channel region of the FET to which the probe molecules are fixed, and a second current value of the channel region of the FET to which the target molecules and the probe molecules that bind to each other in the reaction solution of high ionic concentration are fixed.

In other embodiments of the present invention, methods for detecting biomolecules include: providing a FET comprising a substrate, a source electrode, a drain electrode, a channel region between the source and drain electrodes, and probe molecules fixed to the channel region, wherein the source and drain electrodes are space apart from each other on the substrate; supplying a reference buffer solution of low ionic concentration to the channel region to which the probe molecules are fixed, and measuring a first current value flowing through the channel region; binding the target molecules to the probe molecules by supplying a reaction solution of high ionic concentration containing the target molecules to the channel region to which the probe molecules are fixed; removing the reaction solution of high ionic concentration after reaction by supplying the reference buffer solution of low ionic concentration to the channel region where the target molecules bind to the target molecules, and measuring a second current value flowing through the channel region in the reference buffer solution of low ionic concentration; and detecting the target molecules using a difference between the first and second current values.

Other details of embodiments are included in Mode for Invention and accompanying drawings.

Advantageous Effects

According to an apparatus and method for detecting biomolecules using a field effect transistor (FET) of the present invention, it is possible to detect biomolecules by measuring a variation in a current flowing through a channel region of the FET in a reference buffer solution of low ionic concentration before and after probe molecules and target molecules (i.e., biomolecules) bind to each other in a reaction solution of high ionic strength.

That is, biomolecules can be detected by directly supplying the biomolecules contained in a solution of high ionic strength to a channel region of the FET.

BRIEF DESCRIPTION OF THE DRAWINGS

The accompanying figures are included to provide a further understanding of the present invention, and are incorporated in and constitute a part of this specification. The drawings illustrate exemplary embodiments of the present invention and, together with the description, serve to explain principles of the present invention. In the figures.

MODE FOR THE INVENTION

Figure 1:
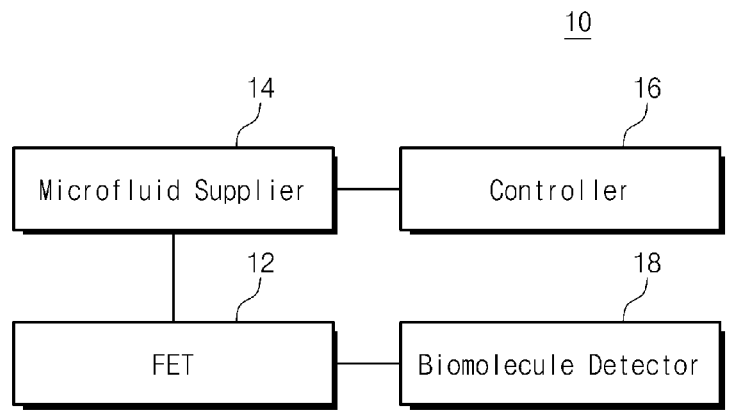
FIG. 1 is a block diagram of an apparatus for detecting biomolecules according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explain a specific exemplary embodiment while not limiting the present invention. The terms of a singular form may include plural forms unless referred to the contrary. The meaning of 'include', 'comprise', 'including', or 'comprising', specifies a property, a region, a fixed number, a step, a process, an element and/or a component but does not exclude other properties, regions, fixed numbers, steps, processes, elements and/or components. It will be understood that when an element such as a layer, film, region, or substrate is referred to as being 'on' another element, it can be directly on the other element or intervening elements may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a semiconductor package region. Thus, this should not be construed as limited to the scope of the present invention.

In the specification, biomolecules are molecules of living organisms, representing specific attributes. The biomolecules have the same meaning as a target molecule or analytes.

Herebelow, an apparatus for detecting biomolecules according to embodiments of the present invention will be more fully described.

Figure 2:
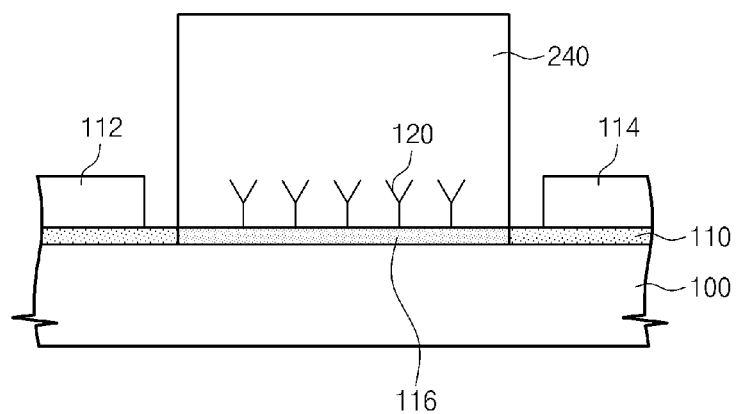
FIG. 2 is a schematic sectional view of the apparatus for detecting biomolecules according to the embodiment of the present invention.

FIG. 1 is a block diagram of an apparatus for detecting biomolecules according to an embodiment of the present invention. FIG. 2 is a schematic sectional view of the apparatus for detecting biomolecules according to the embodiment of the present invention. FIGS. 3A and 3B are schematic plan views of the apparatus for detecting biomolecules according to the embodiment of the present invention.

Referring to FIG. 1, the apparatus (or biosensor, biochip, or microarray) for detecting biomolecules according to the embodiment of the present invention includes a field effect transistor (FET) 12, a microfluid supplier 14, a controller 16, and a biomolecule detector 18.

The FET 12 is a biosensor, which can detect biomolecules according to a variation in a current flowing through a channel region thereof. Probe molecules are fixed to the channel region of the FET 12, and a current value of the channel region varies when target molecules (i.e., biomolecule or analytes) bind to the probe molecules. The intensity of a current flowing through the channel region may vary as a Debye length of a surface charge varies with the ionic strength of a solution provided to the channel region of the FET 12, that is, ion concentration.

The microfluid supplier 14, which is the channel region of the FET 12 to which the probe molecules are fixed, selectively supplies a reference buffer solution of low ionic concentration and a reaction solution of high ionic concentration containing biomolecules. In addition, the microfluid supplier 14 can supply a stabilization buffer solution for stabilizing charges around the probe molecules.

The controller 16 controls a plurality of microfluids to be supplied to the channel region of the FET 12 from the microfluid supplier 14. That is, the controller 16 can supply one of the reference buffer solution of low ionic concentration, the reaction solution of high ionic concentration, and the stabilization buffer solution, to the channel region of the FET 12. Furthermore, the controller 16 can control a supplying sequence and/or supplying duration of the microfluids.

The biomolecule detector 18 can measure a current value that varies depending on the microfluids supplied to the channel region of the FET 12, and thus detects the biomolecules through analysis of the measured current value.

Figure 3:
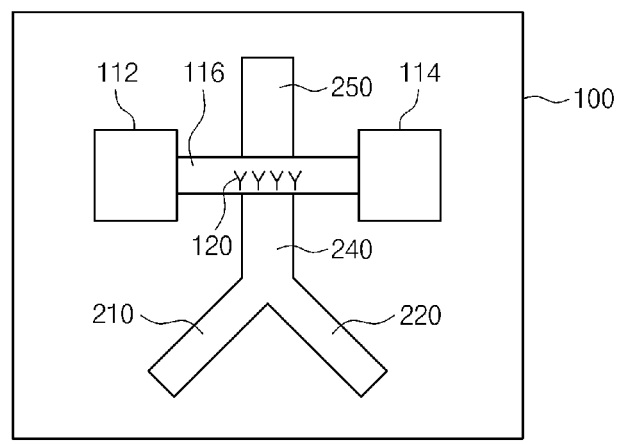
FIGS. 3 and 4 are schematic plan views of the apparatus for detecting biomolecules according to the embodiment of the present invention.
Figure 4:
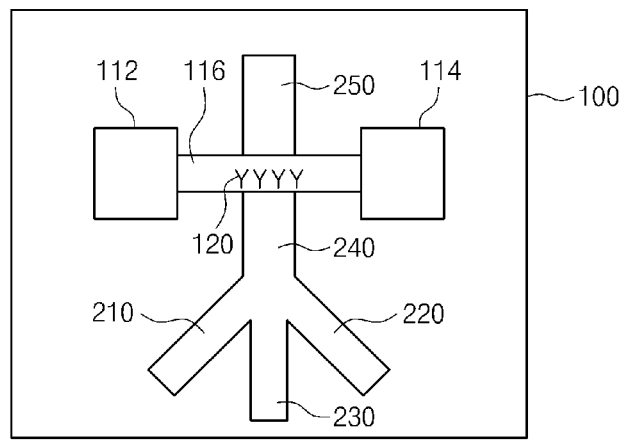

Referring to FIGS. 2, 3 and 4, the FET 12 including an n- or p-type FET includes a substrate 100, a source electrode 112, a drain electrode 114, and a channel region 116.

A bulk semiconductor substrate may be used for the substrate 100 where the FET 12 is formed. Alternatively, a silicon-on-insulation (SOI) substrate may be used as the substrate 100 so as to reduce a leakage current of the FET 12 and increase a driving current. In addition, other substrates formed of silicon oxide, titanium oxide, acryl resin, epoxy resin, polyimide, etc., may be used for the substrate 100.

The source and drain electrodes 112 and 114 may be spaced apart from each other by a predetermined distance on the substrate 100. A voltage may be applied to the source and drain electrodes 112 and 114. The channel region 116 is provided between the source and drain electrodes 112 and 114. Further, a contact layer 110 may be provided under the source and drain electrodes 112 and 114, and electrically connects the source and drain electrodes 112 and 114 to each other.

The channel region 116 of the FET 12 may include an impurity-doped layer, a semiconductor layer, an oxide layer, a compound layer, a carbon nanotube (CNT) or a semiconductor nanowire. In embodiments of the present invention, description will be made on the assumption that the channel region 116 includes a doped layer.

The doped layer may include a diffusion layer formed through impurity diffusion, an ion implantation layer formed through impurity ion implantation, or an epitaxial layer formed through epitaxial growth. The doped layer may have a conductive type complementary to that of the substrate 100. For example, the doped layer may have p-type conductivity if the semiconductor substrate 100 has n-type conductivity.

The surface of the channel region 116 including the doped layer between the source and drain electrodes 112 and 114 may be surface-treated to fix the probe molecules 120. For example, a carboxyl group (—COOH), a thiol group (—SH), a hydroxyl group (—OH), a silane group, an amine group, or an epoxy group may be introduced to the surface of the dope layer that has been surface-treated.

Although it is described that the channel region between source and drain electrodes 112 and 114 may include the doped layer in the embodiment of the present invention, a gate electrode may be provided on the semiconductor substrate 100 between the source and drain electrodes 112 and 114. Alternatively, the source and drain electrodes 112 and 114 may be a doped region formed by doping impurities into the semiconductor substrate 100.

In the FET 12, the probe molecules 120 are fixed on the channel region 116 to detect the biomolecules, i.e., target molecules. The probe molecules 120 may be directly fixed to the surface of the channel region 116 of the FET 12, or may be fixed to the surface of the channel region 116 by using organic molecules as intermediate molecules. The probe molecule 120 may include a protein, a cell, a virus, or a nucleic acid depending on a biomolecule to be detected. In this case, the protein may include any biomolecule such as an antigen, an antibody, a matrix protein, an enzyme, a coenzyme, a ligand, an aptamer, and a receptor or the like, and the nucleic acid may include DNA, RNA, PNA, LNA, or hybrids thereof.

Also, the channel region 116 of the FET 12 to which the probe molecules 120 are fixed may be connected to the microfluid supplier 14 that supplies the microfluids to detect the biomolecules.

The microfluid supplier 14 supplies the respective microfluids, which are used to detect the biomolecules, to the channel region 116 of the FET 12. The microfluid supplier 14 selectively supplies the plurality of microfluids to the FET 12 so as to detect the biomolecules. That is, the microfluid supplier 14 selectively supplies of the reference buffer solution of low ionic concentration, the reaction solution of high ionic concentration containing the biomolecules, and the reference buffer solution of low ionic concentration, to the channel region 116 of the FET 12 in sequence.

The microfluid supplier 14 may include at least one or more fluid channels that respectively supply the plurality of microfluids to the FET 12. The fluid channels may be formed on the substrate 10 where the FET 12 is formed.

To be specific, the microfluid supplier 14 may include a first fluid channel 210, a second fluid channel 220, and a joint channel 240.

The first and second fluid channels 210 and 220, through which different fluids flow respectively, are separated from each other. The joint channel 240 serves as a pathway supplying the fluids flowing through the first and second fluid channels 210 and 220 to the channel region 116 of the FET 12. One end of the joint channel 240 may be connected to the first and second fluid channels 210 and 220, and the other end is connected to the channel region 116 of the FET 12. That is, the first and second channel regions 210 and 220 are divided from the joint channel 240.

In addition, the microfluid supplier 14 may further include a third fluid channel 230 supplying the stabilization buffer solution, as illustrated in FIG. 4. The third fluid channel 230 may be connected to the joint channel 240 together with the first and second fluid channels 210 and 220.

In the embodiments of the present invention, the fluids supplied through the first, second and third fluid channels 210, 220 and 230 may be, for example, the reference buffer solution of low ionic concentration, the reaction solution of high ionic concentration, and the stabilization buffer solution. Each of the first through third fluid channels 210, 220 and 230 may include a one-way valve that is opened toward the channel region 116 of the FET 12 when the solutions are supplied.

Also, the microfluid supplier 14 may include a discharge channel 250 on an opposite side to the joint channel 240, which can discharge the fluids of the first through third fluid channels 210, 220 and 230.

Although it is described that the microfluid supplier 14 is formed on the substrate 10 in the embodiment of the present invention, the present invention is not limited thereto. Thus, the microfluid supplier used in the present invention can variously modify in different forms. For example, the microfluid supplier may be an independent element that is separated from the substrate where the FET is formed.

Figure 5:
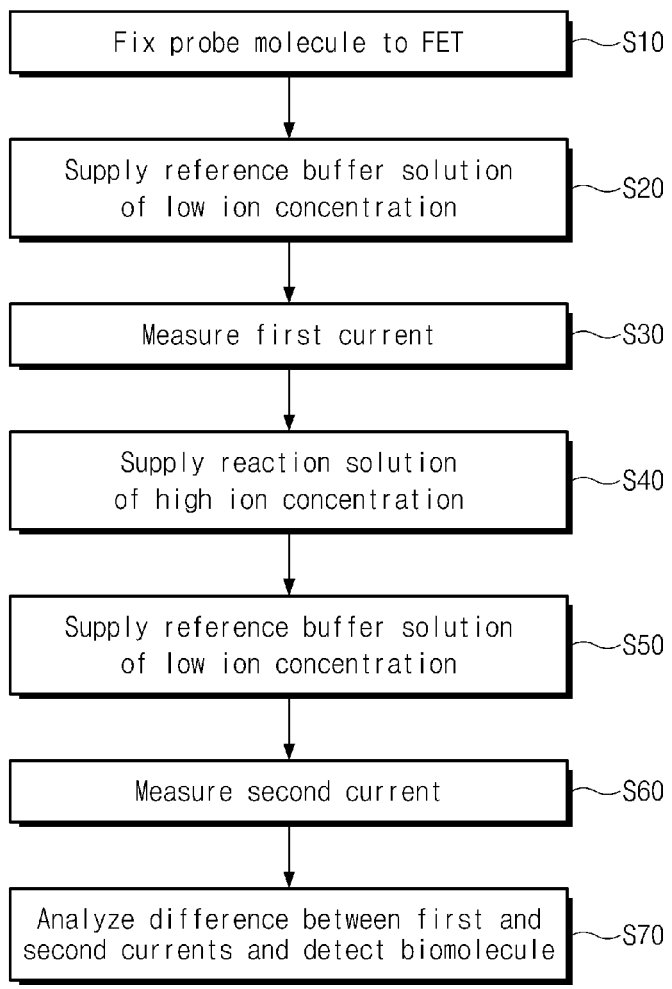
FIG. 5 is a flowchart illustrating a method for detecting biomolecules according to an embodiment of the present invention.

Herebelow, a method for detecting biomolecules according to an embodiment of the present invention will be described with reference to FIG. 5. FIG. 5 is a flowchart illustrating a method for detecting biomolecules according to an embodiment of the present invention.

In operation S10, a FET is prepared to detect biomolecules, and probe molecules are then fixed to a channel region of the FET. That is, the probe molecules may be fixed to the surface of a doped layer of the FET.

In operation S20, a reference buffer solution of low ionic concentration is supplied to the channel region of the FET to which the probe molecules are fixed. The reference buffer solution is a buffer solution of which an ion concentration is relatively low, allowing charges of the probe molecules to have a sufficient Debye length according as the probe molecules bind to the target molecules.

In operation S30, a first current flowing through the channel region to which the probe molecules are fixed is measured by applying a voltage to source and drain electrodes of the FET, in a state where the reference buffer solution is supplied to the channel region of the FET. A current value measured in operation S30 is defined as a first current value.

In operation S40, a reaction solution of high ionic concentration is supplied to the channel region of the FET to which the probe molecules are fixed. The reaction solution of high ionic concentration includes biomolecules to be detected, that is, target molecules (or analytes). The reaction solution of high ionic concentration containing the target molecules is a solution of which an ion concentration is high, for example, blood (or blood serum or plasma), urine, or saliva obtained from living organisms. The reaction solution of high ionic concentration may provide the optimized conditions for binding of the target molecules to the probe molecule in the channel region of the FET. That is, as the reaction solution of high ionic concentration is supplied to the channel region of the FET, the target molecules bind to the probe molecules. Herein, even though the target molecules bind to the probe molecules, a Debye length of a biomolecule charge is shortened due to the high ionic concentration of the reaction solution, which makes it difficult to measure a variation in current flowing through the channel region of the FET.

In operation S50, the reference buffer solution of low ionic concentration is supplied to the channel region of the FET where the target molecules bind to the probe molecules. The reference buffer solution supplied herein may be the same as the reference buffer solution used in operation S20. The reference buffer solution supplied in operation S50 removes the reaction solution of high ionic concentration containing the target molecules unbound to the probe molecules. The reference buffer solution provides a sufficient Debye length to the probe molecules bound to the target molecules, which makes it possible to measure a current variation of the channel region according to the binding of the target molecules.

In operation S60, a second current flowing through the channel region is measured by applying a voltage to the source and drain electrodes of the FET in the reference buffer solution of low ionic concentration. Herein, a current value measured in operation S60 is defined as a second current value.

In operation S70, a difference between the first and second current values is calculated and analyzed, thereby detecting biomolecules. That is, the biomolecules in the reaction solution of high ionic concentration can be detected by analyzing the current value of the channel region in case where the target molecules do not bind to the probe molecules, and the current value of the channel region in case where the target molecules bind to the probe molecules.

Figure 6:
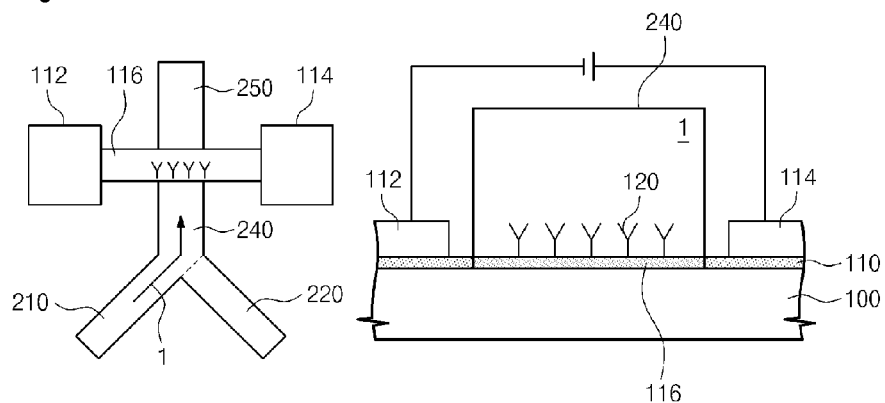
FIGS. 6 through 8 are sectional views illustrating a method for detecting biomolecules in sequence according to an embodiment of the present invention.
Figure 7:
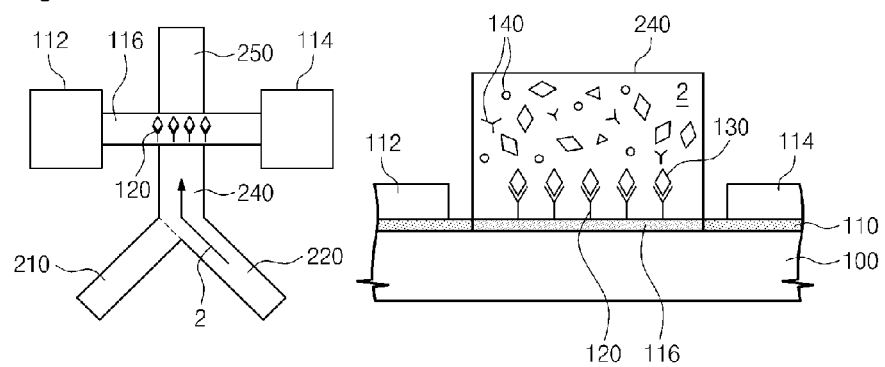
Figure 8:
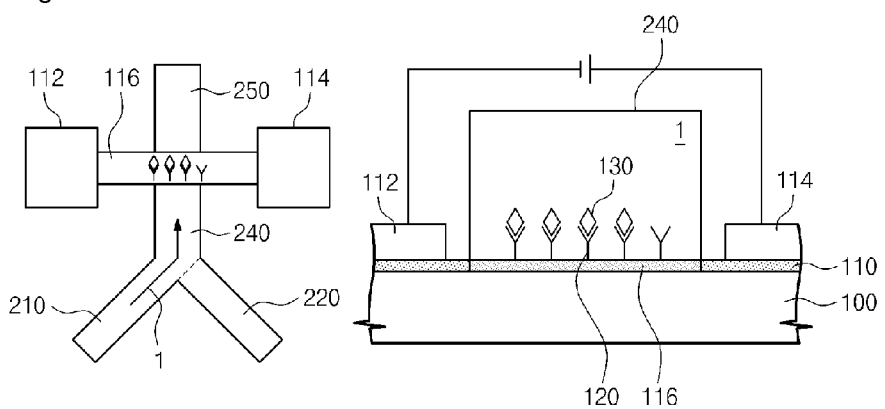

Herebelow, a method for detecting biomolecules using the apparatus for detecting biomolecules of FIG. 1 will be more fully described with reference to FIGS. 6 through 8. FIGS. 6 through 8 are sectional views illustrating the method for detecting biomolecules in sequence according to an embodiment of the present invention.

Referring to FIG. 6, a reference buffer solution 1 of low ionic concentration is supplied to a channel region 116 of a FET to which probe molecules are fixed. A voltage is applied to source and drain electrodes 112 and 114 of the FET to measure a current of the channel region 116. The current measured herein is defined as a first current. To measure the current of the channel region 116, the reference buffer solution 1 of low ionic concentration is supplied, and a saturation current is then measured after a predetermined time elapses.

Here, the probe molecule fixed to the channel region 116 of the FET may include, for example, a protein, a nucleic acid, an organic molecule, or an inorganic molecule. In this case, the protein may include any biomolecule such as an antigen, an antibody, a matrix protein, an enzyme, a coenzyme, or the like, and the nucleic acid may include DNA, RNA, PNA, LNA, or hybrids thereof.

The reference buffer solution 1 of low ionic concentration may be supplied to the channel region 116 of the FET through a first fluid channel 210 and a joint channel 240. The reference buffer solution of low ionic concentration is a buffer solution of which an ion concentration is relatively low, allowing charges of the probe molecules to have a sufficient Debye length according as the probe molecules bind to the target molecules. The reference buffer solution allows a predetermined pH to be maintained. For example, the reference buffer solution 1 may include NaCl, KCl, sodium phosphate of which concentration ranges from few μM to several tens of mM, or may include ions similar to blood (blood serum or plasma), urine, or saliva obtained from living organisms.

The probe molecules 120 fixed to the channel region 116 of the FET may have positive or negative charges on the surface of the doped channel region 116 in the reference buffer solution of low ionic concentration. When a voltage is applied to the source and drain electrodes 112 and 114, a current flows between the source and drain electrodes 112 and 114 through the doped channel region 116. That is, a voltage is applied to the source and drain electrodes 112 and 114, holes or electrons existing in the doped channel region 116 as carriers are affected by the ionic strength of the reference buffer solution 1, thereby changing the value of current flowing through the doped channel region 116.

The value of the current flowing through the doped channel region 116 may vary depending on the quantity of a net charge (positive or negative charge) of the probe molecule 120 fixed to the surface of the doped channel region 116. In other words, the probe molecules 120 may be fixed to the surface of the channel region 116 in such a way to have positive or negative charges. By contrast, neutral molecules may be fixed to the surface of the doped channel region 116. As the quantity of the net charge (positive or negative charge) fixed to the surface of the doped channel region 116 increases, the amount of carriers, i.e., the amount of holes or electrons on the surface of the doped channel region 116 may vary, leading to a variation in a current flowing through the doped channel region 116.

Referring to FIG. 7, thereafter, a reaction solution 2 of high ionic concentration containing target molecules 130 is supplied to the channel region 116 of the FET to which the probe molecules 120 are fixed, so that the target molecules 130 bind to the prove molecules 120. The target molecules 130 bound to the probe molecules 120 fixed to the channel region 116 of the FET provide a new positive or negative charge to the surface of the doped channel region 116. The value of current flowing through the doped channel region 116 may vary with the quantity of the net charge (positive or negative charge) of the target molecule 130 bound to the probe molecule 120 fixed to the surface of the doped channel region 116. That is, the target molecules 130 bound to the probe molecules 120 have a negative or positive charge on the surface of the doped channel region 116 according to pH of the reference buffer solution. According to the quantity of positive or negative charge of the target molecule 130 newly supplied to the surface of the doped channel region 116, the carrier type, i.e., hole or electron, in the doped channel region 116 may be changed, which leads to a variation in current flowing through the doped channel region 116 between the source and drain electrodes 112 and 114.

The reaction solution 2 of high ionic concentration may be supplied to the channel region 116 of the FET via the second fluid channel 220 and the joint channel 240. The reaction solution 2 of high ionic concentration containing the target molecules 130 is a solution of high ionic concentration, for example, blood (blood serum or plasma), urine, or saliva obtained from living organisms. The reaction solution 2 of high ionic concentration may include not only the target molecules 120, but also nonspecific molecules 140 that do not bind to the probe molecules 120.

As the reaction solution of high ionic concentration is supplied to the channel region 116 of the FET, the target molecules 130 bind to the probe molecules 120 in the doped channel region 116 of the FET. In the channel region 116, the target molecules 130 bind to the probe molecules 120 through well-known binding mechanisms such as nucleic acid hybridization, antigen-antibody reaction, and enzyme binding reaction. The reaction solution of high ionic concentration can optimize the binding of the target molecules to the probe molecules 120.

For reference, the binding force between the probe molecule 120 and the target molecule 130 is weak in the reaction solution of low ionic concentration containing the target molecules 130. Therefore, when the reaction solution 2 of low ionic concentration is washed through supplying the reference buffer solution 1 of low ionic concentration after the target molecules 130 bind to the probe molecules 120, the bonds between the probe molecule 120 and the target molecule 130 may be broken. Thus, the reaction solution should be carefully selected in this case.

Referring to FIG. 8, the reference buffer solution 1 of low ionic concentration is supplied to the channel region 116 of the FET where the target molecules 130 bind to the probe molecules 120, and then a current flowing through the channel region 116 of the FET is measured. Herein, the measured current is defined as a second current value. To measure the current of the channel region 116, the reference buffer solution 1 of low ionic concentration is supplied first, and a saturation current is then measured after the current value of the channel region 116 is stabilized.

Here, as the reference buffer solution 1 is supplied to the channel region 116 of the FET, the reaction solution 2 of high ionic concentration, which contains the target molecules 130 not bound to the probe molecules 120 and the nonspecific molecules 140, is removed. When the reaction solution 2 of high ionic concentration is removed by the reference buffer solution 1, the binding of the target molecules 130 to the probe molecules 120 is still maintained in the channel region 116 of the FET.

After the second current value is measured, a difference between the first and second current values is analyzed to detect the target molecule 130. That is, it is possible to detect the target molecules 130 in the reaction solution 2 of high ionic concentration because the variation in current value before and after the target molecule 130 bind to the probe molecule 120 through the reference buffer solution of low ionic concentration.

Herebelow, a method for detecting biomolecules using an apparatus for detecting biomolecules according to another embodiment of the present invention will be described with reference to FIGS. 6A through 6E. FIGS. 6A through 6E are sectional views illustrating a method for detecting biomolecules in sequence according to another embodiment of the present invention.

The method for detecting biomolecules according to another embodiment of the present invention further includes stabilizing a surrounding atmosphere of a probe molecule 120 fixed to a channel region 116 by supplying a stabilization solution to the channel region 116 of a FET before or after a reference buffer solution 1 of low ionic concentration is supplied to the channel region 116.

Figure 9:
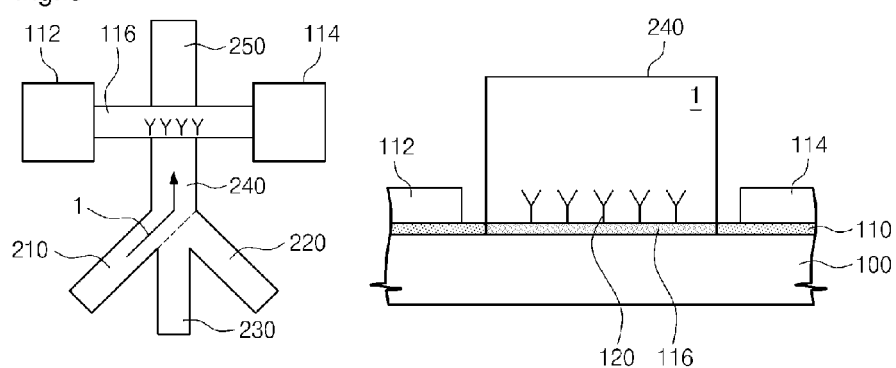
FIGS. 9 through 13 are sectional views illustrating a method for detecting biomolecules in sequence according to another embodiment of the present invention.

Referring to FIG. 9, the reference buffer solution 1 of low ionic concentration is supplied to the channel region 116 of the FET fixed to the probe molecule 120. The reference buffer solution 1 of low ionic concentration is a buffer solution of which an ion concentration is relatively low, allowing charges of the probe molecules to have a sufficient Debye length according as the probe molecules 130 bind to the probe molecules 120. The reference buffer solution allows a predetermined pH to be maintained.

Figure 10:
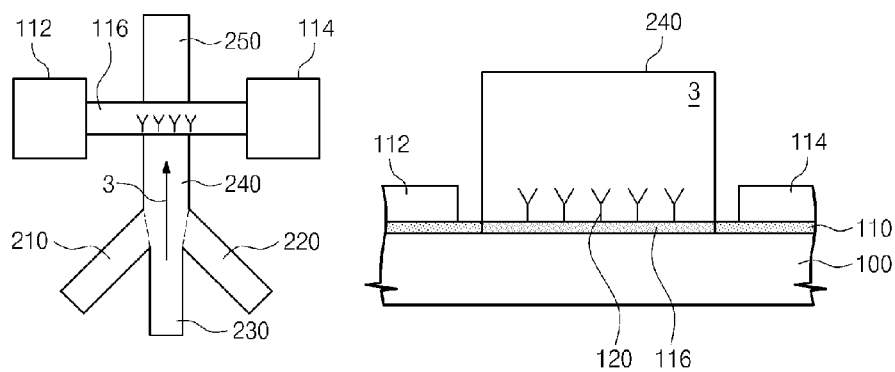

Referring to FIG. 10, a stabilization solution 3 is supplied to the channel region 116 of the FET to which the probe molecules 120 are fixed, thus removing the reference buffer solution of low ionic concentration from the channel region 116.

That is, charges of the probe molecules 120 fixed to the channel region 116 may change the Debye length due to high ionic concentration as well as the binding of the probe molecules to the target molecules 130, and thus it is necessary to stabilize ionic properties around the probe molecules 120. Therefore, the stabilization solution 3 of high ionic concentration is supplied after the reference buffer solution of low ionic concentration is supplied.

The stabilization buffer solution 3 is a buffer solution having an ionic strength similar to that of the reaction solution 2 of high ionic concentration containing the target molecules 130. The stabilization buffer solution 3 may be supplied to the channel region 116 of the FET through a third fluid channel and a joint channel, independently of the first and second fluid channels.

Figure 11:
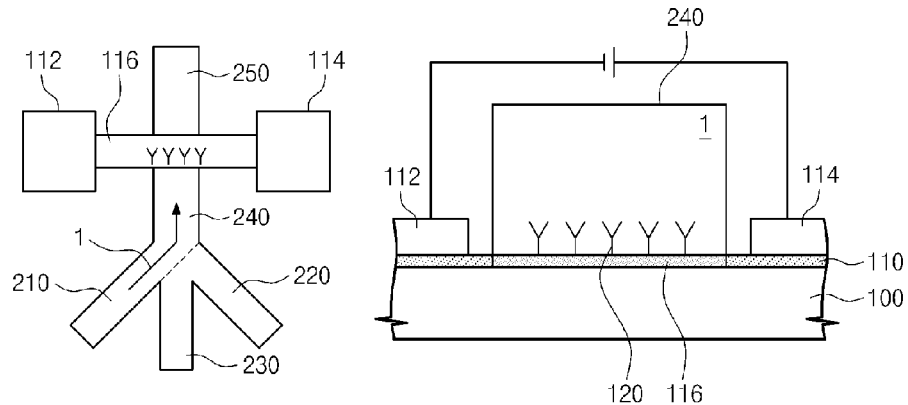

Referring to FIG. 11, the surrounding atmosphere of the probe molecules 120 is stabilized by the stabilization buffer solution 3, and thereafter the reference buffer solution 1 of low ionic concentration may be supplied to the channel region 116 of the FET again.

As the reference buffer solution 1 of low ionic concentration is supplied, the stabilization buffer solution 30 is removed from the channel region 116. Afterwards, in a state where the surrounding atmosphere of the probe molecules 120 is stabilized, a current flowing through the channel region 116 is measured by applying a voltage to the source and drain electrodes 112 and 114 of the FET. Accordingly, a saturation current flowing through the channel region 116 in the reference buffer solution 1 of low ionic concentration is measured. A current measured herein may be defined as the first current value.

As illustrated in FIGS. 6A through 6C, the supplying of the reference buffer solution 1 and the stabilization buffer solution 3 may be performed once or more before the reaction solution 2 of high ionic concentration is supplied.

Figure 12:
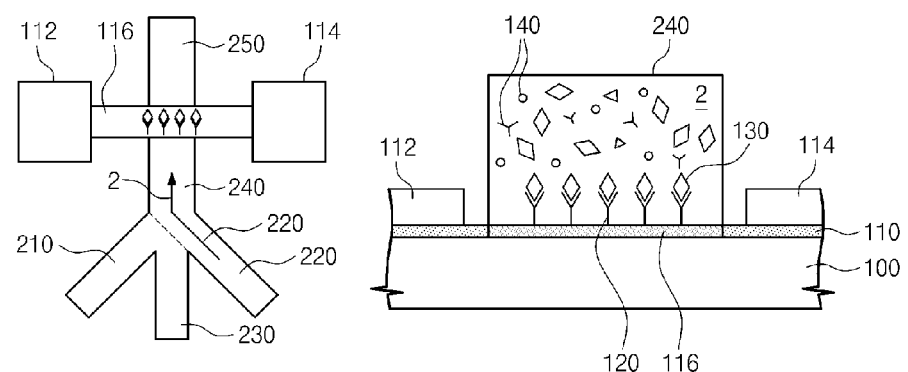

Subsequently, referring to FIG. 12, the reaction solution 2 of high ionic concentration containing the target molecules 130 is supplied to the channel region 116 of the FET to which the probe molecules 120 are fixed. The reaction solution of high ionic concentration containing the target molecules 130 is a solution of high ionic concentration, for example, blood (blood serum or plasma), urine, or saliva obtained from living organisms. The reaction solution 2 of high ionic concentration may include not only the target molecules 120, but also nonspecific molecules 140 that do not bind to the probe molecules 120.

As the reaction solution 2 of high ionic concentration is supplied to the channel region 116, the target molecules 130 bind to the probe molecules 120 in the channel region 116 of the FET.

After the reaction solution 2 of high ionic concentration is supplied, a stabilization buffer solution (not shown) may be supplied. That is, the binding of the target molecules 130 to the probe molecules 120 is maintained for a sufficient time, and then the stabilization buffer solution (not shown) may be supplied to the channel region 116 of the FET. Alternatively, it is also possible to bind the target molecules 130 to the probe molecules 120 by alternatively supplying the reaction solution 2 of high ionic concentration and the stabilization buffer solution (not shown).

Figure 13:
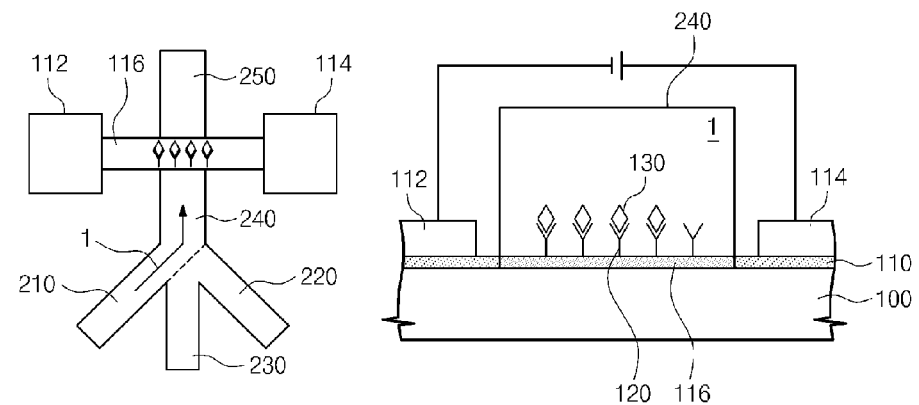

Thereafter, referring to FIG. 13, the reference buffer solution 1 of low ionic concentration is supplied to the channel region 116 of the FET where the target molecules 130 bind to the probe molecules 120, and a current flowing through the channel region 116 is then measured. Here, as the reference buffer solution 1 of low ionic concentration is supplied, the reaction solution 2 of high ionic concentration containing nonspecific molecules 140 and the target molecules 130 not bound to the probe molecules 120 is removed. Afterwards, a saturation current is measured in a state where the current value of the channel region 116 is stabilized. The current measured herein may be defined as a second current value.

The second current value is a current value resulted from the binding of the target molecules 130 to the probe molecules 120 in the reference buffer solution 1 of low ionic concentration. Therefore, the target molecules 130 can be detected through a difference between the first and second current values of the probe molecules 120.

As illustrated in another embodiment of the present invention, a reference current value can be more accurately measured by supplying the stabilization buffer solution 3 to the channel region 116 of the FET before the first current value resulted from the probe molecules 120 is measured using the reference buffer solution 1. Consequently, it is possible to improve the reliability of the method for detecting biomolecules.

Figures 14, 15:
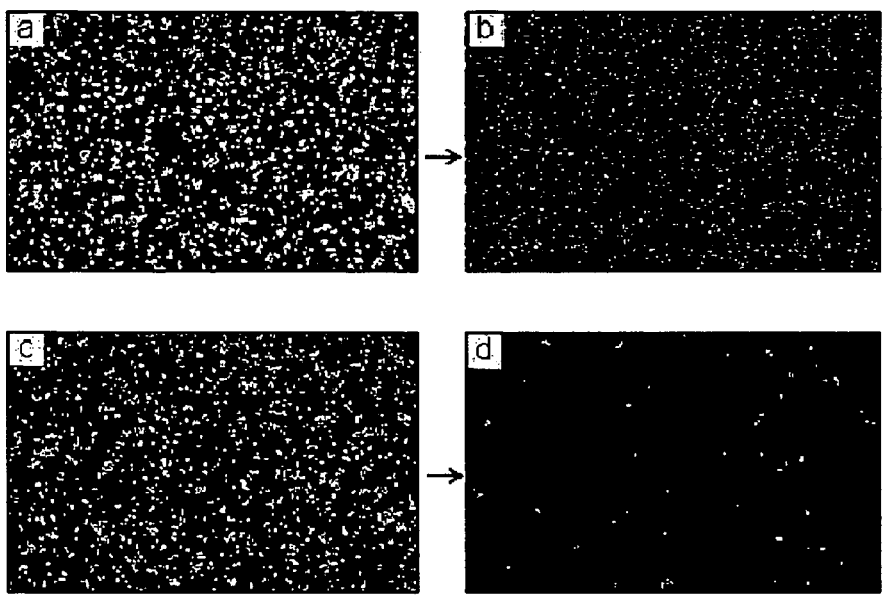
FIG. 14 illustrates scanning electron microscope (SEM) views showing binding states of target molecules to probe molecules when reaction solutions are removed with a reference buffer solution, after the target molecules bind to the probe molecules in the respective reaction solutions having different ion concentrations.
FIG. 15 is a quantification table showing remaining degrees of probe and target molecules bound to each other, when a FET is washed after the target molecules bind to the probe molecules.

FIG. 14 illustrates scanning electron microscope (SEM) views showing binding states of target molecules to probe molecules when reaction solutions are removed with a reference buffer solution after the target molecules bind to the probe molecules in the respective reaction solutions having different ion concentrations. FIG. 15 is a quantification table showing remaining degrees of probe molecules and target molecules bound to each other, when a reaction solution is removed from a silicon substrate after the target molecule binds to the probe molecule.

A prostate specific antigen (PSA) was used as the target molecule, and a monoclonal anti-PSA was used as the probe molecule. 5 µM phosphate buffer (PB) solution was used as the reference buffer solution of low ionic concentration, 5 µM PB solution containing PSA was used as the reaction solution of high ionic concentration, and 10 mM phosphate buffered saline (PBS) containing PSA was used as the reaction solution of high ionic concentration. Furthermore, the anti-PSA on the surface of the channel region were bound to polyclonal anti-PSA Au Nps conjugates in order to indicate the remaining degree of the probe molecule and the target molecule.

Referring to the substrates a and b in FIGS. 7 and 8, when the reaction solution of high ionic strength (10 mM PBS) is removed by supplying the reference buffer solution of low ionic strength (5 µM PB solution) to the channel region of the FET where the anti-PSA was bound to the PSA, after binding the anti-PSA to the PSA in the reaction solution of high ionic concentration (10 mM PBS), it can be observed that most of the bound anti-PSA and PSA remains.

On the contrary, referring to the substrates c and d in FIGS. 7 and 8, when the reaction solution of low ionic strength (5 µM PB solution) is removed by supplying the reference buffer solution of low ionic strength (5 µM PB solution) to the silicon substrate where the anti-PSA was bound to the PSA, after binding the anti-PSA to the PSA in the reaction solution of low ionic concentration (5 µM PB solution), it can be observed that most of the bound anti-PSA and PSA are removed.

Accordingly, even though the reaction solution is washed using the reference buffer solution of low ionic concentration after the target molecules bind to the probe molecules in the reaction solution of high ionic concentration, the binding degree can be maintained about 100%. Therefore, it is possible to detect biomolecules by measuring a variation in current flowing through the channel region of the FET in the reference buffer solution of low ionic concentration before and after the target molecules bind to the probe molecules in the reaction solution of high ionic concentration.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A method for detecting biomolecules, the method comprising:
    providing a FET comprising a substrate, a source electrode, a drain electrode, a channel region between the source and drain electrodes, and probe molecules fixed to the channel region, wherein the source and drain electrodes are space apart from each other on the substrate;
    supplying a reference buffer solution of low ionic concentration to the channel region to which the probe molecules are fixed, and measuring a first current value flowing through the channel region when a reference buffer solution of low ionic concentration is supplied to the channel region to which the probe molecules are fixed;
    binding the target molecules to the probe molecules by supplying a reaction solution of high ionic concentration containing the target molecules to the channel region to which the probe molecules are fixed;
    removing the reaction solution of high ionic concentration after reaction by supplying the reference buffer solution of low ionic concentration to the channel region where the target molecules bind to the probe molecules;
    measuring a second current value flowing through the channel region when the reference buffer solution of low ionic concentration is supplied to the channel region where the target molecules bind to the probe molecules; and
    detecting the target molecules using a difference between the first and second current values.

2. The method of claim 1, further comprising, before the measuring of the first current value, supplying a reference buffer solution of low ionic concentration, and supplying a stabilization solution.

3. The method of claim 2, wherein the supplying of the reference buffer solution of low ionic concentration and the supplying the stabilization solution are repeated once or more.

4. The method of claim 2, wherein the reaction solution of high ionic concentration includes blood, blood serum, blood plasma, urine, saliva, or a high ionic concentration solution, which contains the target molecules.

5. The method of claim 2, wherein the stabilization solution has an ionic strength or an ion similar to the reaction solution of high ionic concentration.

6. The method of claim 2, wherein the measuring of the first or second current value of the channel region comprises measuring a saturation current of the channel region after supplying the reference buffer solution of low ionic concentration.

7. The method of claim 1, wherein the channel region of the FET comprises an impurity-doped layer, a semiconductor layer, an oxide layer, a compound layer, a metal layer, a carbon nanotube (CNT), or a semiconductor nanowire.

8. The method of claim 1, wherein the probe molecule or the target molecule is selected from the group consisting of a nucleic acid, a cell, a virus, a protein, an organic molecule, an inorganic molecule, and a biomolecule.

9. The method of claim 8, wherein the nucleic acid is selected from the group consisting of DNA, RNA, PNA, LNA, and hybrids thereof.

10. The method of claim 8, wherein the protein is selected from the group consisting of an enzyme, a substrate, an antigen, an antibody, a ligand, an aptamer, and a receptor.

11. The method of claim 8, wherein the binding of the target molecules to the probe molecules comprises a nucleic acid hybridization, an antigen-antibody reaction, an enzyme binding reaction.

\* \* \* \* \*